US011013497B2

(12) United States Patent
Suzuki et al.

(10) Patent No.: US 11,013,497 B2
(45) Date of Patent: May 25, 2021

(54) PROGRAM FOR PREDICTING DAY OF OVULATION AND METHOD OF PREDICTING THE SAME

(71) Applicant: MTI Ltd., Tokyo (JP)

(72) Inventors: Kenta Suzuki, Tokyo (JP); Ichiro Igari, Tokyo (JP)

(73) Assignee: MTI LTD., Tokyo (JP)

(*) Notice: Subject to any disclaimer, the term of this patent is extended or adjusted under 35 U.S.C. 154(b) by 271 days.

(21) Appl. No.: 15/129,249

(22) PCT Filed: Mar. 26, 2015

(86) PCT No.: PCT/JP2015/059398
§ 371 (c)(1),
(2) Date: Sep. 26, 2016

(87) PCT Pub. No.: WO2015/147174
PCT Pub. Date: Oct. 1, 2015

(65) Prior Publication Data
US 2018/0228474 A1 Aug. 16, 2018

(30) Foreign Application Priority Data
Mar. 28, 2014 (JP) .............................. JP2014-069044

(51) Int. Cl.
A61B 10/00 (2006.01)
G16H 50/50 (2018.01)

(52) U.S. Cl.
CPC ......... A61B 10/0012 (2013.01); G16H 50/50 (2018.01); A61B 2010/0019 (2013.01); A61B 2010/0029 (2013.01)

(58) Field of Classification Search
CPC ........ A61B 10/0012; A61B 2010/0019; A61B 2010/0029; A61B 2503/12;
(Continued)

(56) References Cited

U.S. PATENT DOCUMENTS 4,465,077 A * 8/1984 Schneider .......... A61B 10/0012
600/551
5,606,535 A * 2/1997 Lynn .................. A61B 10/0012
368/10
(Continued)

FOREIGN PATENT DOCUMENTS

CN 1297343 A 5/2001
ES 2366929 T3 10/2011
(Continued)

OTHER PUBLICATIONS

Wilcox, Allen J., et al. The Timing of The 'Fertile Window' In the Menstrual Cycle: Day Specific Estimates From a Prospective Study. BMJ: British Medical Journal, vol. 321, No. 7271 (Nov. 18, 2000), pp. 1259-1262 [online], [retrieved on Aug. 8, 2018]. Retrieved from the Internet <URL: http://www.jstor.org/stable/25226217>.*
(Continued)

Primary Examiner — Matthew Kremer
Assistant Examiner — Samuel C Kim
(74) Attorney, Agent, or Firm — Taft Stettinius & Hollister LLP; Stephen F. Rost

(57) ABSTRACT

An object is to provide programs for reliable predictions of the day of ovulation. A process is executed in a program for predicting a day of ovulation on a computer, the process including calculating a predicted ovulation day data corresponding to a particular menstrual cycle by applying the particular menstrual cycle to a relationship between a period between a menstrual day and a day of ovulation and an average length of a menstrual cycle, the relationship being estimated based on data of a plurality of persons which have been previously obtained.

6 Claims, 9 Drawing Sheets

(58) Field of Classification Search
CPC .. A61B 2505/07; G16H 50/50; A61D 17/002; A01K 29/005
USPC .......................................................... 600/55
See application file for complete search history.

(56) References Cited

U.S. PATENT DOCUMENTS

| | | | | |
|---|---|---|---|---|
| 6,278,999 | B1* | 8/2001 | Knapp | G06F 19/3418 |
| 6,522,912 | B1 | 2/2003 | Nakatani et al. | |
| 2002/0095297 | A1* | 7/2002 | Hasegawa | G10L 15/02 704/500 |
| 2004/0193069 | A1 | 9/2004 | Takehara | |
| 2013/0137940 | A1* | 5/2013 | Schafer | A61B 10/0012 600/301 |
| 2015/0112706 | A1* | 4/2015 | Baron | G06F 19/00 705/2 |
| 2016/0296210 | A1* | 10/2016 | Matsushima | G16H 10/60 |

FOREIGN PATENT DOCUMENTS

| | | | | |
|---|---|---|---|---|
| JP | 2004290335 | A | 10/2004 | |
| JP | 2010012091 | A | 1/2010 | |
| JP | 2011062322 | A | 3/2011 | |
| JP | 5179799 | B | 1/2013 | |
| WO | 93/07578 | A1 | 4/1993 | |
| WO | WO 9307578 | A1* | 4/1993 | ......... A61B 10/0012 |
| WO | 01/19251 | A1 | 3/2001 | |
| WO | WO 0119251 | A1* | 3/2001 | ......... A61B 10/0012 |

OTHER PUBLICATIONS

Arevalo, Marcos, et al. A Fixed Formula to Define the Fertile Window of the Menstrual Cycle as the Bases of a Simple Method of Natural Family Planning. Contraception, vol. 60, No. 6 (Dec. 1999), pp. 357-360 [online], [retrieved on Aug. 8, 2018]. Retrieved from the internet <URL: https://www.sciencedirect.com/science/article/pii/S0010782499001067?via%>.*
Wilcox, Allen J., et al. Timing of Sexual Intercourse in Relation to Ovulation—Effects on the Probability of conception, Survival of the Pregnancy, and Sex of the Baby. New England Journal of Medicine, vol. 333, No. 23 (Dec. 1995), pp. 1517-1521 [online], [retrieved on Sep. 10, 2018], DOI: 10.1056/NEJM199512073332301.*
Wilcox Allen J, Dunson David, Baird Donna Day. The timing of the "fertile window" in the menstrual cycle: day specific estimates from a prospective study BMJ 2000; 321 :1259 (Year: 2000).*
Mcintosh, J. E., et al. (1980). Predicting the Luteinizing Hormone Surge: Relationship Between the Duration of the Follicular and Luteal Phases and the Length of the Human Menstrual Cycle. Fertility and Sterility, 34(2), 125-130. doi: 10.1016/s0015-0282(16)44894-6 (Year: 1980).*
International Search Report (Translated into English), pp. 1-2, dated Jun. 23, 2015, Japan Patent Office.
A. J Wilcox: "The timing of the 'fertile window' in the menstrual cycle: day speciic estimates from a prospective study." BMJ, vol. 321, No. 7271, Nov. 18, 2000, pp. 1259-1262, XP055428572, ISSN: 0959-8138.
Aravalo: "A Fixed Formula to Define the Fertile Window of that Menstrual Cycle as the Basis of a Simple Method of Natural Family Planning," Jan. 1, 1999, XP055428469.
European Search Report, European Patant Office, Dec. 6, 2017, pp. 1-10.
Pokrovsky VI Encyclopedic Dictionary of Medical Terms, Second Edition in vol. 1, Moscow, "Medicine", 2001, p. 475; and transaltion.
Russian Federation; Non Final Office Action (with translation); dated Dec. 18, 2018.
The State Intellectual Property Office of People's Republic of China; Chinese First Office Action; dated Jan. 3, 2019; pp. 1-155.
Russian Patent and Trademark Office, Russia; Russian Office Action (with Translastion); dated Dec. 13, 2018; pp. 1-10.

* cited by examiner

PROGRAM FOR PREDICTING DAY OF OVULATION AND METHOD OF PREDICTING THE SAME

This application is a U.S. national stage application under 35 U.S.C. § 371 of PCT International Application Serial No. PCT/JP2015/059398, which has an international filing date of Mar. 26, 2015, designates the United States of America. and claims the benefit of Japanese Patent Application No. 2014-069044, which was filed on Mar. 28, 2014. The disclosures of each of these prior applications are hereby expressly incorporated by reference in their entirety.

TECHNICAL FIELD

The present invention relates to techniques to predict the day of ovulation.

BACKGROUND ART

Various methods have been investigated to predict the day of ovulation. They include long-term and immediate prediction methods.

Long-term prediction methods provide predictions of the first day of menstruation and the day of ovulation in the future, based on data of several past menstrual cycles. More specifically, long term methods include the Knaus-Ogino method (the calendar rhythm method) and the midpoint method. The midpoint method adds the number of days equal to half the average length of a menstrual cycle to the first day of the last menstruation to use it as an anticipated day of ovulation.

Immediate prediction methods predict that the day of ovulation is coming or ovulation has occurred based on physical data. More specifically, predictions are made using basal body temperature (the coverline calculation method) or using change in physical condition (e.g., cervical mucus is examined).

Other techniques to predict a menstruation day and the day of ovulation include, for example, the one described in Patent literature 1.

RELATED ART DOCUMENT(S)

Patent Literature

Patent literature 1: Japanese Patent No. 5179799

SUMMARY OF THE INVENTION

Problems to be Solved by the Invention

All of the aforementioned prediction methods are, however, difficult to provide a reliable prediction of the day of ovulation. For example, in the Knaus-Ogino method, the day of ovulation is predicted under the assumption that a period between the day of ovulation and the first day of the next menstruation is constant (14 days). The period between the day of ovulation and the first day of the next menstruation differs from woman to woman as the length of a menstrual cycle does. It is thus difficult to provide a reliable prediction of the day of ovulation using the Knaus-Ogino method. Furthermore, transition from follicular to luteal phase typically occurs after ovulation. The coverline calculation method can thus be used only to grasp the day of ovulation afterward.

In addition, it is desired to provide reliable predictions of the day of ovulation even for a woman who does not have sufficient data of her menstrual cycle and the day of ovulation.

The present invention was made to solve the aforementioned problems and an object thereof is to provide techniques to provide reliable predictions of the day of ovulation.

Means to Solve the Problem

In order to solve the aforementioned problems, a process is executed in a program for predicting a day of ovulation in the present invention on a computer, the process including: calculation a predicted ovulation clay data corresponding to a particular menstrual cycle by applying the particular menstrual cycle to a relationship between a period between a menstrual day and a day of ovulation and an average length of a menstrual cycle, the relationship being estimated based on data of a plurality of persons which have been previously obtained.

Furthermore, in order to solve the aforementioned problems, a method of predicting a day of ovulation in the present invention calculates a predicted ovulation day data corresponding to a particular menstrual cycle by applying the particular menstrual cycle to a relationship between a period between a menstrual day and a day of ovulation and an average length of a menstrual cycle, the relationship being estimated based on data of a plurality of persons which have been previously obtained.

Effect of the Invention

According to the present invention, by using an average tendency related to the day of ovulation in a population of women with the same average length of their menstrual cycle, it is possible to provide reliable predictions of the day of ovulation based on a woman's menstrual cycle.

MODES FOR CARRYING OUT THE INVENTION

<Configuration Applicable to all Embodiments>

Figure 1:
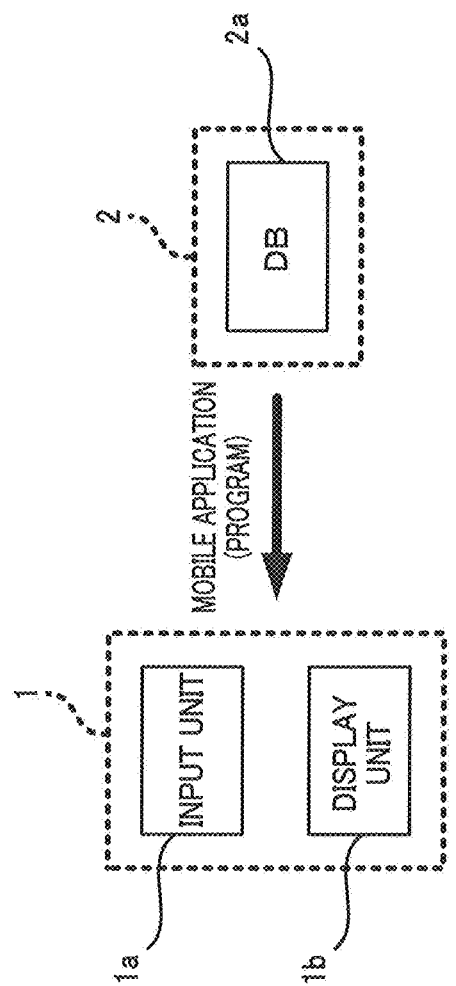
FIG. 1 is a schematic view showing a configuration applicable to all embodiments.
Figure 1:

Referring to FIG. 1, a configuration applicable to all embodiments is described.

A user terminal 1 is a mobile terminal (e.g., a smartphone or a tablet computer) or a personal computer owned by a person. The user terminal 1 includes an input unit 1a and a display unit 1b. The user terminal 1 is an example of a "computer."

A server 2 includes a database (DB) 2a in which data obtained from users are recorded and managed. Furthermore, the server 2 builds a predetermined program using the data stored on the database 2a.

Examples of the data recorded in the database 2a are the first day(s) of menstruation, the day(s) of ovulation, and the day(s) with sexual activity. These data are available via, for example, menstrual day prediction services or pregnancy support services for personal use, provided as a mobile application or a web page. These data have also sometimes been collected for conventional medical investigations, but the number is only dozens to hundreds. In contrast, the server 2 can collect data on a larger scale (at least thousands to tens of thousands) than before, using a service or services as above. Diagrams (graphs) referred to in the following embodiments show the results obtained on the basis of such large-scale data. Such large-scale data is an example of "data of a plurality of persons which have been previously obtained" in the present invention.

The program built by the server 2 is implemented as, for example, an application software. A user can download this software as a mobile application to the user terminal 1. The user can execute the program of the present invention by running the mobile application. Hereinafter, details of this program are described in each embodiment.

Although an example where a program is executed on the user terminal 1 is described in each embodiment, the computer on which the program is to be executed is not limited to the user terminal 1. For example, the user terminal 1 may serve only as input means and display means and the server 2 may execute the program based on an input from the user terminal 1. Alternatively, one or more programs may be executed on the user terminal 1 and the remaining program(s) may be executed on the server 2.

First Embodiment

Figure 2:
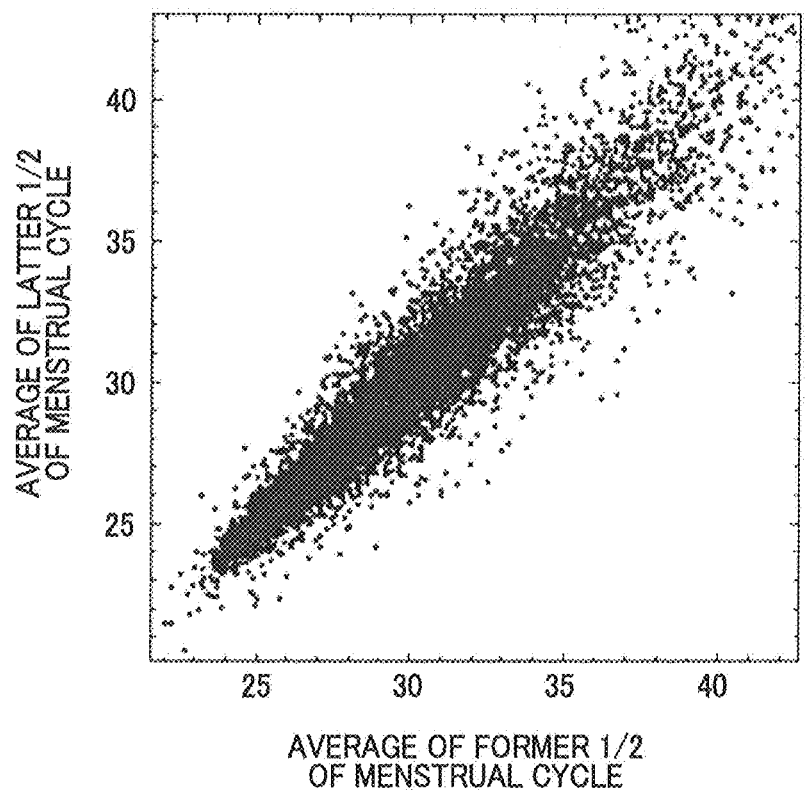
FIG. 2 is a diagram used to supplement the description of a first embodiment.
Figure 3:
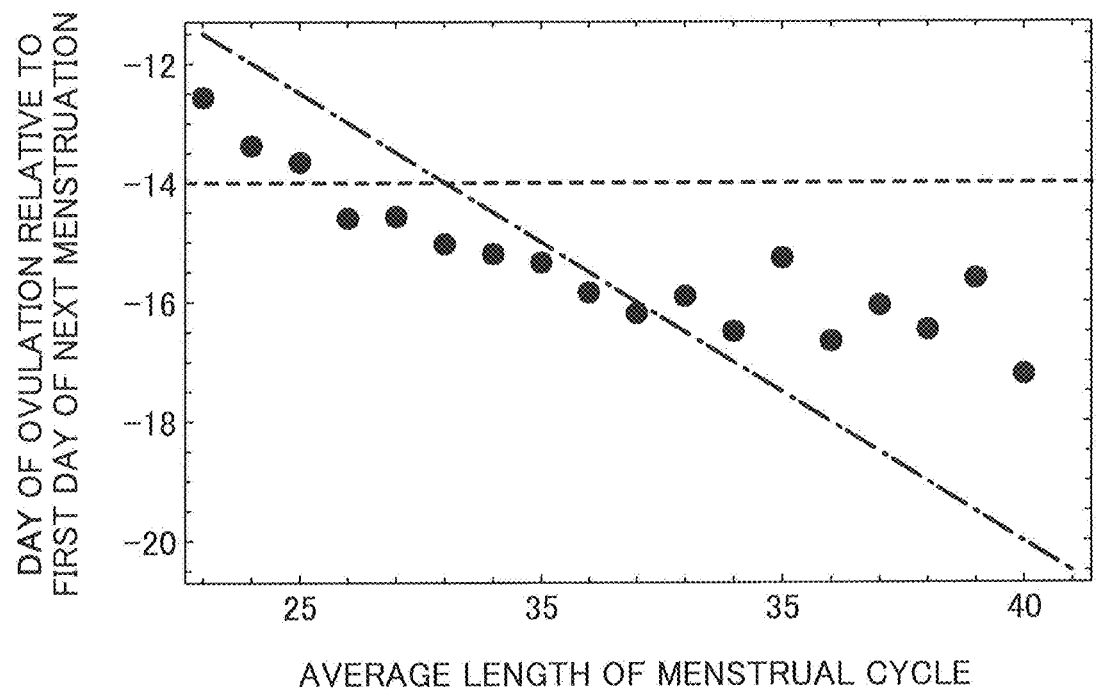
FIG. 3 is a diagram used to supplement the description of the first embodiment.
Figure 4:
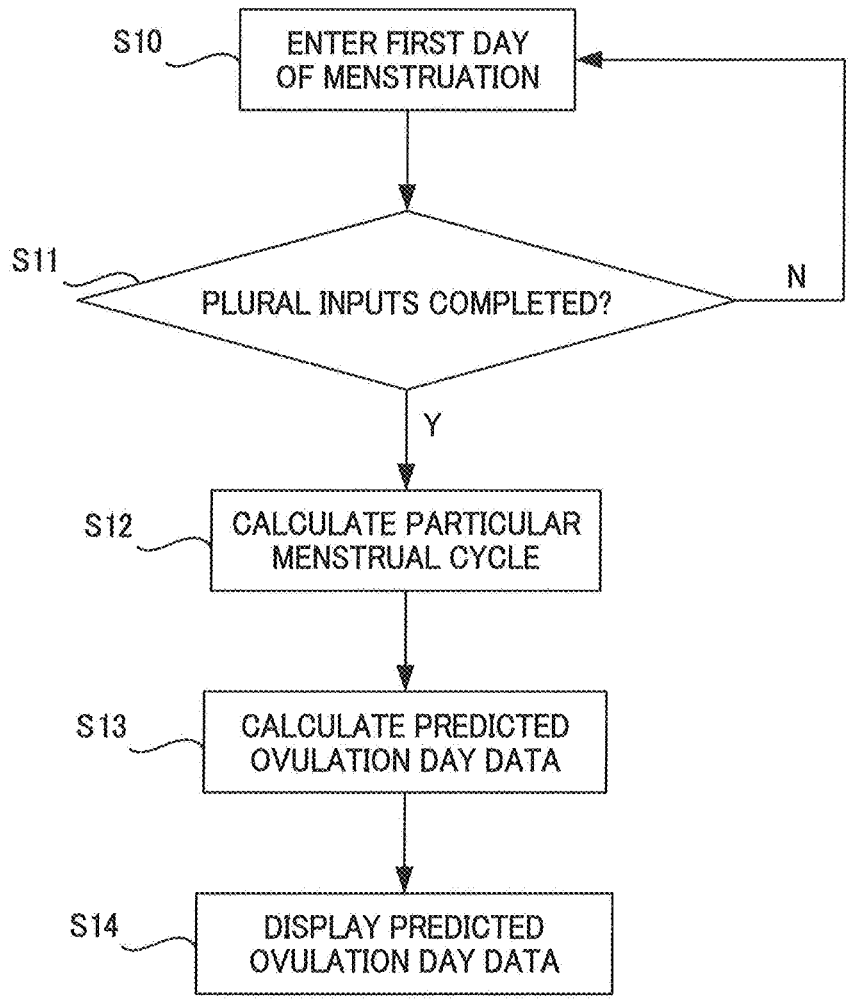
FIG. 4 is a flowchart showing a process of a program according to the first embodiment.

Referring to FIGS. 2 to 4, a program according to a first embodiment is described. This embodiment describes an example where to day of ovulation of a user is predicted based on an average length of her menstrual cycle.

A process of calculating a particular menstrual cycle is executed in the program according to this embodiment on the user terminal 1 based on menstruation data which have been received a plurality of times through the input unit 1a.

The "menstrual day data" is data related to menstrual days of the user. For example, the menstrual day data contains the first day of menstruation (date). Alternatively, the menstrual day data can contain the number of days of a menstrual cycle if the cycle is known.

The user enters the menstrual day data through the input unit 1a of the user terminal 1. An input operation is performed using touch keys of the user terminal 1 or the voice of the user.

If the user enters the first days of, for example, three menstrual cycles, executed in the program on the user terminal 1 is a process of calculating two menstrual cycles by determining the number of days from the first day of a first menstruation to the first day of a second menstruation and the number of days from the first clay of the second menstruation to the first day of a third menstruation. A process of calculating an average length of the menstrual cycle is then executed in the program on the user terminal 1 by averaging the lengths of two menstrual cycles.

Alternatively, executed in the program on the user terminal 1 is a process of calculating a menstrual cycle by applying a past menstrual cycle or cycles (which can be determined from at least two menstrual day data entered) of the user to a statistical model based on large-scale data to weight the menstrual cycles using a specific weight (for example, the last menstrual cycle is assigned with "1" and the menstrual cycle just before the last one is assigned with "0.9").

The "particular menstrual cycle" as used in this embodiment conceptually includes an average length of the menstrual cycle of a user who has entered her menstrual day data and an average length, of the menstrual cycle calculated using a statistical model.

It should be noted that a user who knows her particular menstrual cycle in advance is only required to enter a value of that cycle once.

Executed in the program on the user terminal 1 is a process of calculating a predicted ovulation day data corresponding to a particular menstrual cycle by applying the particular menstrual cycle to a relationship between a period between a menstrual day and a day of ovulation and the average length of the menstrual cycle, estimated based on the data of a plurality of persons which have been previously obtained. The "period between the menstrual day and the day of ovulation" conceptually includes the number of days from the first day of menstruation prior to the clay of ovulation to the day of ovulation in a menstrual cycle and the number of days from the day of ovulation to the first day of the next menstruation.

The "predicted ovulation day data" is data related to prediction of the day of ovulation. The predicted ovulation day data is calculated as, for example, a numerical value reckoned from the menstrual day, such as plus 10 days from the menstrual day prior to the predicted day of ovulation in a menstrual cycle or minus 10 days from a next predicted menstrual day, or calculated as a date such as what day of what month. The "predicted menstrual day" is the first clay of future menstruation predicted by adding the particular menstrual cycle to the first day of previous menstruation.

Referring to FIGS. 2 and 3, in calculating the predicted ovulation day data of a user, the use of the menstrual cycle (particular menstrual cycle) of the user and a relational expression between the period between the menstrual day and the day of ovulation and the average length of the menstrual cycle is described.

FIG. 2 is a graph showing the regularity of a menstrual cycle of an individual. The horizontal axis represents an average (in the number of days) of the former halves of the menstrual cycles for a plurality of menstrual cycles. The vertical axis represents an average (in the number of days) of the latter halves of the menstrual cycles for the plurality of menstrual cycles. The points on the graph represent a distribution of individuals who have the data of their twelve or more menstrual cycles.

As apparent from the graph, a strong correlation is found between the past menstrual cycles and the future menstrual cycles. In other words, it can be considered that the menstrual cycle (average length of the menstrual cycle) of an individual is generally constant.

FIG. 3 is a graph showing a relationship between the day of ovulation and the average length of the menstrual cycle. The horizontal axis represents the average length of the menstrual cycle. The vertical axis represents the day of ovulation relative to the first day of the next menstruation.

Each point shown on the graph represents an average value for the day of ovulation relative to the first day of the next menstruation in a plurality of persons having the same average length of their menstrual cycle. The broken line represents the day of ovulation relative to the first day of the next menstruation according to the Knaus-Ogino method (i.e., fixed 14 days regardless of the difference in average lengths of menstrual cycles). The dot-dash line represents the day of ovulation relative to the first day of the next menstruation according to the midpoint method.

As apparent from this graph, the day of ovulation predicted using the conventional methods (the Knaus-Ogino method and the midpoint method) is significantly away from the day of ovulation actually obtained.

The present inventors had conceived that, based on the findings about the relationship between the period between the menstrual day and the day of ovulation and the average length of the menstrual cycle estimated from large-scale data of the plurality of persons as shown in FIG. 3, a reliable prediction of the day of ovulation can be made by applying a menstrual cycle (which is generally constant) of an individual to the relationship described above.

More specifically, the server 2 in this embodiment estimates in advance a relational equation (hereinafter, sometimes referred to as a "relational equation S") for the period between the menstrual day and the day of ovulation and the average length of the menstrual cycle. As a specific example, the server 2 estimates the relational equation S according to a distribution of the average values of the days of ovulation of the plurality of persons having the same average length of their menstrual cycle shown in FIG. 3 The estimated relational equation S is incorporated into the program.

The relational equation S based on the distribution of the average values shown in FIG. 3 can be obtained by least square approximation of the plotted data to a straight or curved line. For example, if the data is approximated by a quadratic curve, the relational equation S can be given as, $f(x)=ax^2+bx+c$. In the equation, x represents a particular menstrual cycle, f(x) represents a predicted ovulation day data, for an average length of the menstrual cycle x, and a, b, and e are constants.

It should be noted that the relational equation S is not limited to the one estimated based on the distribution of the average values. The relational equation S can be estimated based on, for example, a distribution of medians.

A process of calculating the predicted ovulation day data of the user by substituting (applying) the particular menstrual cycle x for (to) the relational equation S is executed in the program on the user terminal 1. The predicted ovulation day data thus calculated is reliable because it is based on an average tendency of the day of ovulation of the women having the same menstrual cycle.

The calculation of the predicted ovulation day data is not limited to the one performed using the relational equation S. For example, the server 2 builds, in advance, a relationship between the period between the menstrual day and the day of ovulation and the average length of the menstrual cycle obtained from the large-scale data, as a table data. A process of calculating the predicted ovulation day data by adapting (applying) the particular menstrual cycle to the table data is executed in the program on the user terminal 1.

Furthermore, a process of displaying the predicted ovulation day data on the display unit 1b can be executed in the program according to this embodiment on the user terminal 1. The predicted ovulation day data can be displayed as a date (what day of what month) of the predicted day of ovulation or the number of days (how many days lie ahead) to the predicted day of ovulation. The user can visually know the predicted day of ovulation when the predicted ovulation day data thus calculated is displayed on the display unit 1b.

The means to present the predicted ovulation day data to the user is not limited to the display. For example, when the user terminal 1 has an audio function, a process of notifying the predicted ovulation day data with sound can be executed in the program. Alternatively, when the user terminal 1 has a communication function using, for example, entails, a process of notifying the predicted ovulation day data using an email can be executed in the program. It should be noted that, in the program of this embodiment, the process of displaying the predicted ovulation day data is not essential.

Next, referring to FIG. 4, an example is described where the program according to this embodiment is executed on the user terminal 1. Described herein is a case where a user uses the software containing the program according to this embodiment for the first time. The user is assumed not to have records such as her menstrual cycles. Furthermore, a mobile application with the program according to this embodiment has downloaded to the user terminal 1.

When menstruation begins, the user starts the mobile application on the user terminal 1 and enters the first day of menstruation (S10). The user repeats entering the first day of menstruation a plurality of times (twice or more) (S11).

If the plural inputs of the first day of menstruation have been completed (Y at S11), the user terminal 1 calculates a menstrual cycle (particular menstrual cycle) of the user from the plurality of first days of menstruation (menstrual day data) entered at S11 (S12).

The user terminal 1 substitutes the menstrual cycle calculated at S12 for the relational equation S estimated in advance for the period between the menstrual day and the day of ovulation and the average length of the menstrual cycle to calculate the predicted ovulation day data of the user (S13).

The user terminal 1 displays the predicted ovulation day data calculated at S13 on the display unit 1b (S14).

As described above, with the program according to this embodiment, even for users who don't have sufficient data on their day of ovulation and menstrual day, it is possible to provide reliable predictions of the day of ovulation by using an average tendency (the estimated relational equation S) of the day of ovulation in a population of women having the same menstrual cycle. Besides, the program according to this embodiment contributes to improving the probability of pregnancy because it can provide such reliable predictions in advance (prior to the day of ovulation).

Second Embodiment

Figure 5:
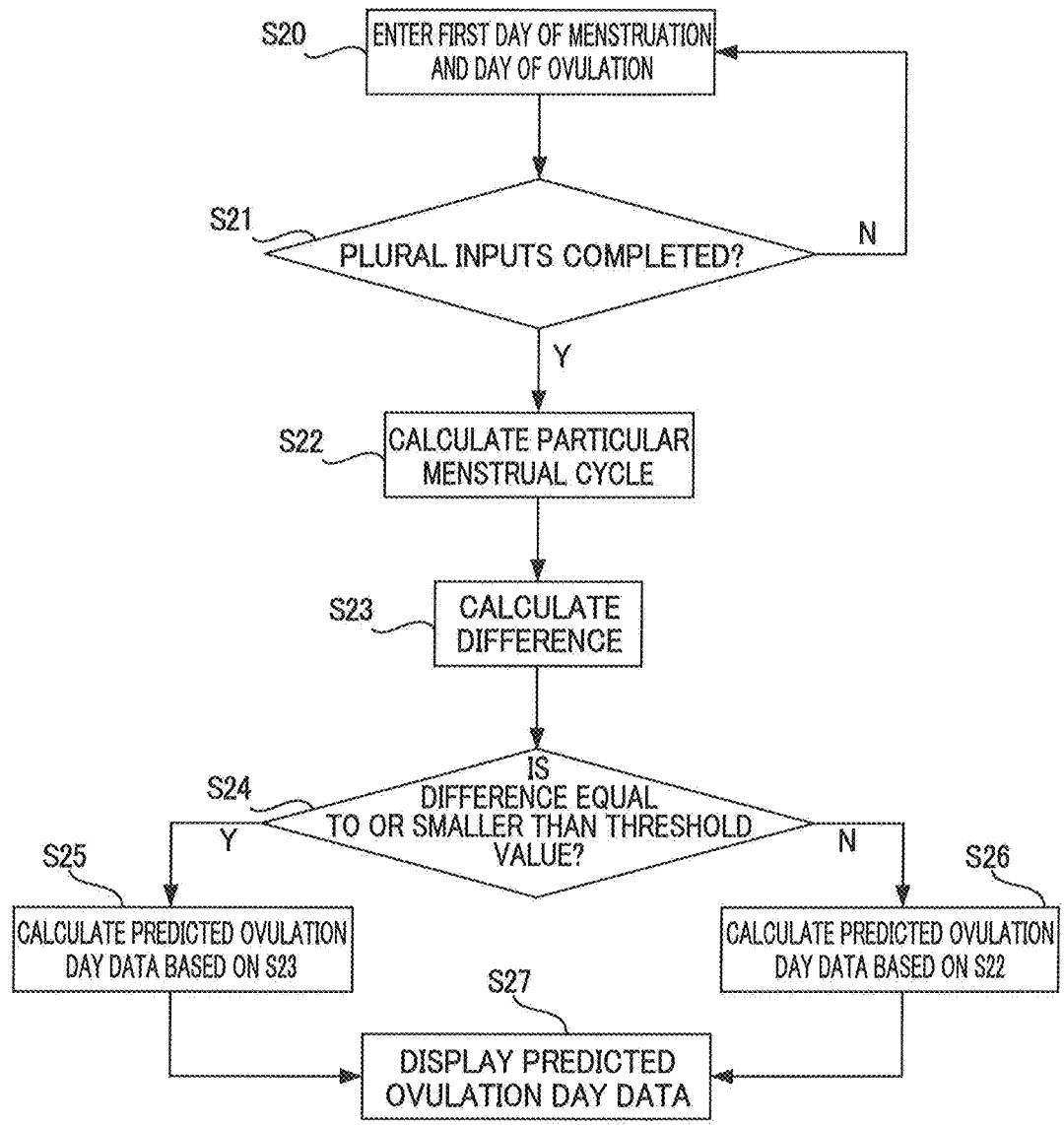
FIG. 5 is a flowchart showing a process of a program according to a second embodiment.

Referring to FIG. 5, a program according to a second embodiment is described. The period between the menstrual day and the day of ovulation may differ from woman to woman in the population of women having the same menstrual cycle. This embodiment describes prediction of the day of ovulation considering such individual differences. Detailed descriptions may be omitted for components and parts similar to those in the first embodiment.

Executed in the program according to this embodiment on the user terminal 1 is a process of calculating a plurality of periods between the menstrual day and the day of ovulation based on ovulation day data entered multiple times through the input unit 1a and the menstrual day data to calculate a difference D between a maximum value and a minimum value of the period.

The "ovulation day data" is data related to the day of ovulation of the user. The ovulation day data is, for example, a date of ovulation determined using a medical procedure. Alternatively, when the day of ovulation is predicted using the coverline calculation method, or the like, the ovulation day data can be the number of days such as a certain day or days after the menstrual day. The "maximum value (of the period)" is the number of days of the longest period between the menstrual day and the day of ovulation. The "minimum value of the period" is the number of days of the shortest period between the menstrual day and the day of ovulation. The "difference D between the maximum value and the minimum value of the period" is, for example, a difference between the maximum number of days and the minimum number of days among the numbers of days from the day of ovulation and the first day of the following menstruation (or the numbers of days from the first day of menstruation prior to the day of ovulation to the day of ovulation), which have been calculated a plurality of times.

According to an analysis of large-scale data, the period between the menstrual day and the day of ovulation less likely varies significantly when focused on a given individual. Based on this finding, when the aforementioned difference D is large, a possible cause would be a wrong input of data or the aforementioned period is deviated from the average tendency of the large-scale data on which the prediction of the day of ovulation is based, which can be considered to be less reliable. In such cases, it is highly possible that a prediction of an exact day of ovulation is difficult even when the menstrual day data and the ovulation day data entered are used. On the other hand, when the aforementioned difference D is small, it can be considered that the reliability of the ovulation day data entered is high. In such cases, a more accurate prediction of the day of ovulation appropriate for the tendency of a given individual can be made using the ovulation day data entered.

Accordingly, in calculating the predicted ovulation day data, when the difference D is equal to or smaller than a threshold value, a process of calculating the predicted ovulation day data is executed in the program on the user terminal 1, based on a plurality of periods between the menstrual day and the day of ovulation. As a specific example, executed in the program on the user terminal 1 is a process of calculating an average value of the calculated plurality of periods between the menstrual day and the day of ovulation to provide this average value as the predicted ovulation day data.

On the other hand, when the difference D is larger than the threshold value (or when only one ovulation day data is present), a process of calculating the predicted ovulation day data is executed in the program on the user terminal 1 using a calculation process (a process using the relational equation S and the particular menstrual cycle) similar to the one in the first embodiment.

The threshold value is a value that is used as a criterion to determine whether the data entered by the user is used to calculate the predicted ovulation day data. Any value can be set for the threshold value based on the result(s) of analysis for the large-scale data.

Next, referring to FIG. 5, an example is described where the program according to this embodiment is executed on the user terminal 1.

When menstruation begins, the user starts the mobile application on the user terminal 1 and enters the first day of menstruation. When the day of ovulation has been determined, the user starts the mobile application on the user terminal 1 and enters the day of ovulation (S20). The user repeats entering the first day of menstruation and the day of ovulation a plurality of times (e.g., three times for the first day of menstruation and twice for the day of ovulation) (S21).

If the plural inputs have been completed (Y at S21), the user terminal 1 calculates a menstrual cycle (particular menstrual cycle) of the user from the plurality of first days, of menstruation (menstrual day data) entered at S21 (S22).

Furthermore, the user terminal 1 calculates a plurality of periods between the menstrual day and the day of ovulation based on the first days of menstruation and the days of ovulation, which have been entered a plurality of times at S21, to calculate a difference D between a maximum value and a minimum value of the period (S23).

When the difference D calculated at S23 is equal to or smaller than a threshold value (Y at S24), the user terminal 1 calculates the predicted ovulation day data of the user based on the plurality of periods between the menstrual day and the day of ovulation obtained at S23 (S25).

On the other hand, when the difference D calculated at S23 is larger than the threshold value (N at S24), the user terminal 1 substitutes the menstrual cycle calculated at S22 for the rotational equation S between the period between the menstrual day and the day of ovulation and the average length of the menstrual cycle, which have been estimated in advance, to calculate the predicted ovulation day data of the user (S26).

The user terminal 1 displays the predicted ovulation day data calculated at S25 or S26 on the display unit 1b (S27).

While the example where the particular menstrual cycle is calculated in advance is described with reference to FIG. 5, the present invention is not limited thereto. The particular menstrual cycle can be calculated only when the difference D calculated at S23 is determined to be larger than the threshold value.

As described above, the program according to this embodiment can provide more reliable predictions of the day of ovulation while considering personal differences, by using the ovulation day data. Accordingly, it is beneficial for users who enter the ovulation day data obtained using medical means or the like.

Third Embodiment

Figure 6:
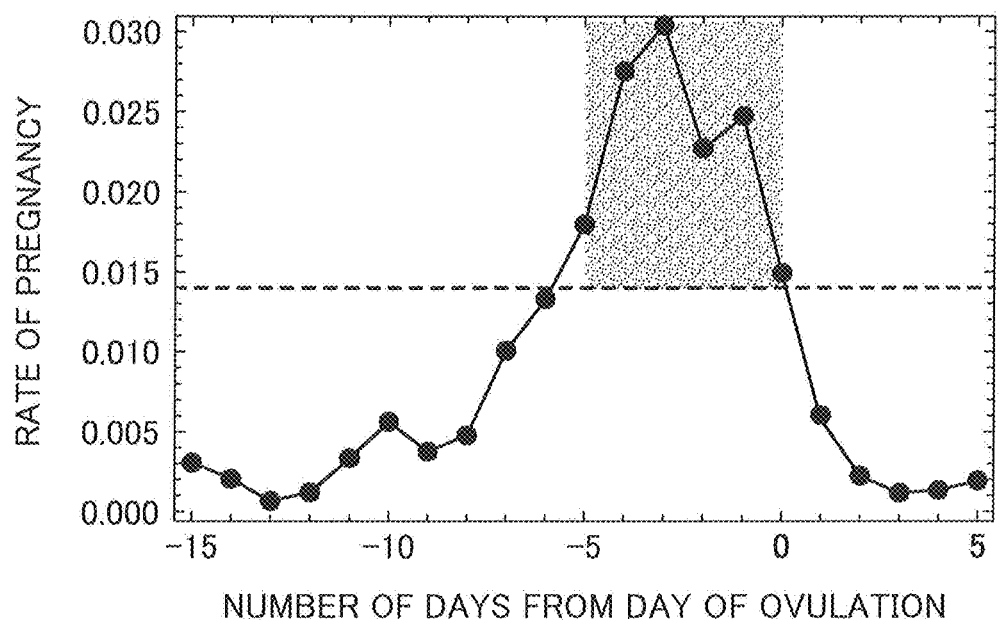
FIG. 6 is a diagram used to supplement the description of a third embodiment.
Figure 7:
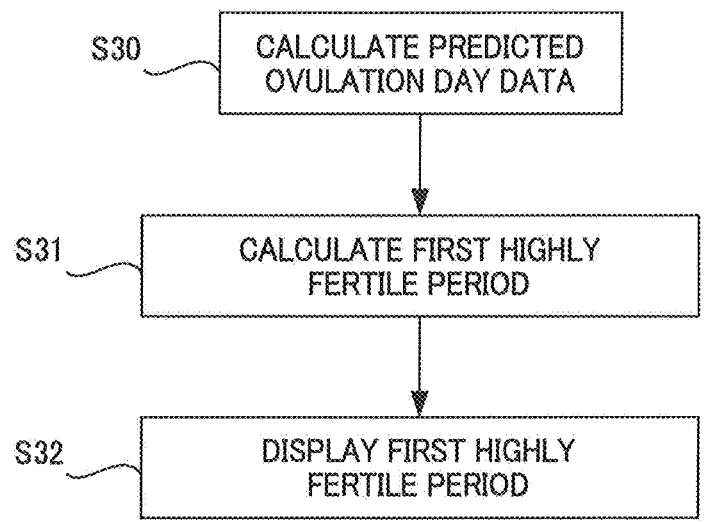
FIG. 7 is a flowchart showing a process of a program according to the third embodiment.

Referring to FIGS. 6 and 7, a program according to a third embodiment is described. From the predicted ovulation day data which have been calculated, the user can know an approximate highly fertile period. This embodiment describes an example where a more reliable highly fertile period (first highly fertile period) is calculated. Detailed descriptions may be omitted for components and parts similar to those in the first and second embodiments.

Executed in the program according to this embodiment on the user terminal 1 is a process of calculating the first highly fertile period based on data on a rate of pregnancy around the day of ovulation, which are based on the data of a plurality of persons which have been previously obtained, as well as the predicted ovulation day data which have been calculated.

The "rate of pregnancy" is a percentage of the number of women who actually get pregnant relative to the number of women with sexual activity on a certain day (for example, the day of ovulation). A "rate of pregnancy around the day of ovulation" is a rate of pregnancy obtained for days around the day of ovulation.

FIG. 6 a graph showing the rate of pregnancy around the day of ovulation. The vertical axis represents the rate of pregnancy and the horizontal axis represents the number of days reckoned from the day of ovulation (0). According to this graph, it can be seen that the rate of pregnancy rises several days before the day of ovulation. The data shown on this graph is an example of "data related to a rate of pregnancy around the day of ovulation."

A process of calculating the first highly fertile period by applying, the predicted ovulation day data which have been calculated to the data shown on the graph is executed in the program on the user terminal 1. As a specific example, with the day of ovulation denoted by "0" on the aforementioned graph used as the predicted day of ovulation, the first highly fertile period can be calculated by determining a period during which the rate of pregnancy or higher than a predetermined rate of pregnancy around the reference day.

Furthermore, a process of displaying the calculated first highly fertile period on the display unit 1b is executed in the program according to this embodiment on the user terminal 1. How the first highly fertile period is displayed is not specifically limited. Furthermore, the first highly fertile period may be displayed along with the predicted ovulation day data calculated in the first and second embodiments, or only either of them may be displayed. Similar to the predicted ovulation day data, means to present the first highly fertile period to the user is not limited to the display.

Next, referring to FIG. 7, an example is described where the program according to this embodiment is executed on the user terminal 1. Described herein is an example where the process in the third embodiment is added to the process in the first embodiment.

The user terminal 1 calculates the predicted ovulation day data using processes similar to those in the first embodiments (see, S10 to S13) (S30).

The user terminal 1 calculates the first highly fertile period by applying the predicted ovulation day data calculated at S30 to the data on the rate of pregnancy around the ovulation day based on the data of a plurality of persons which have been previously obtained (S31).

The user terminal 1 displays the predicted ovulation day data calculated at S30 and the first highly fertile period calculated at S31 on the display unit 1b (S32).

With the program according to this embodiment, the first highly fertile period can be calculated based on the predicted ovulation day data which have been calculated. The user can improve the probability of pregnancy by obtaining the data related to the first highly fertile period in addition to the predicted ovulation day data.

Fourth Embodiment

Figure 8:
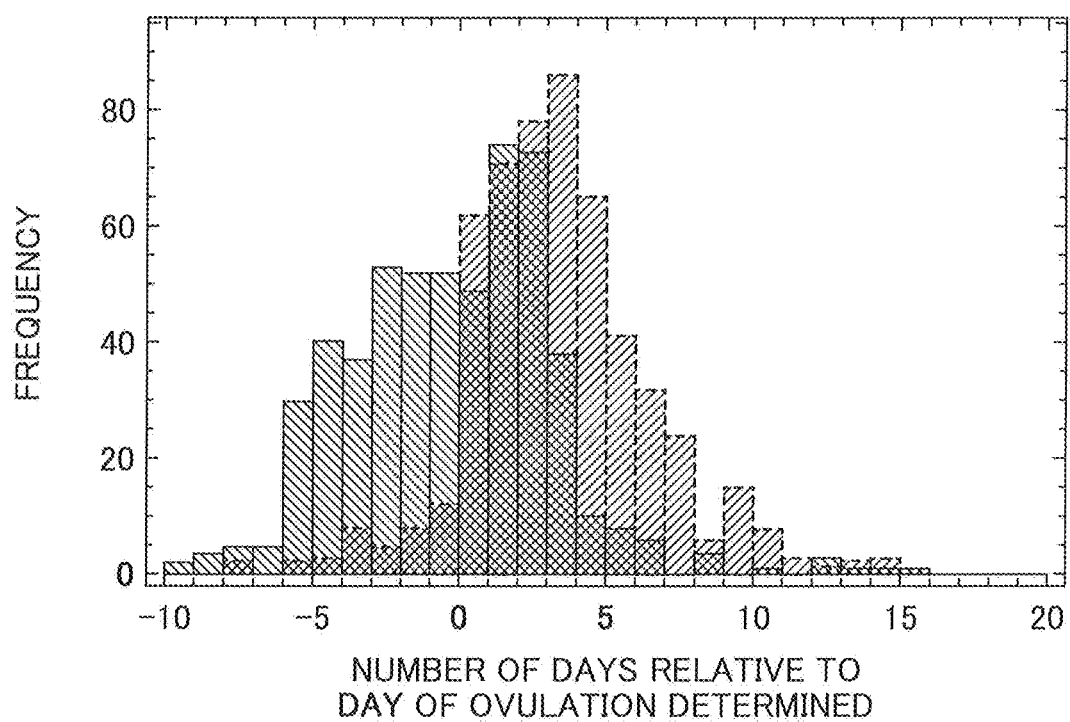
FIG. 8 is a diagram used to supplement the description of a fourth embodiment.
Figure 9:
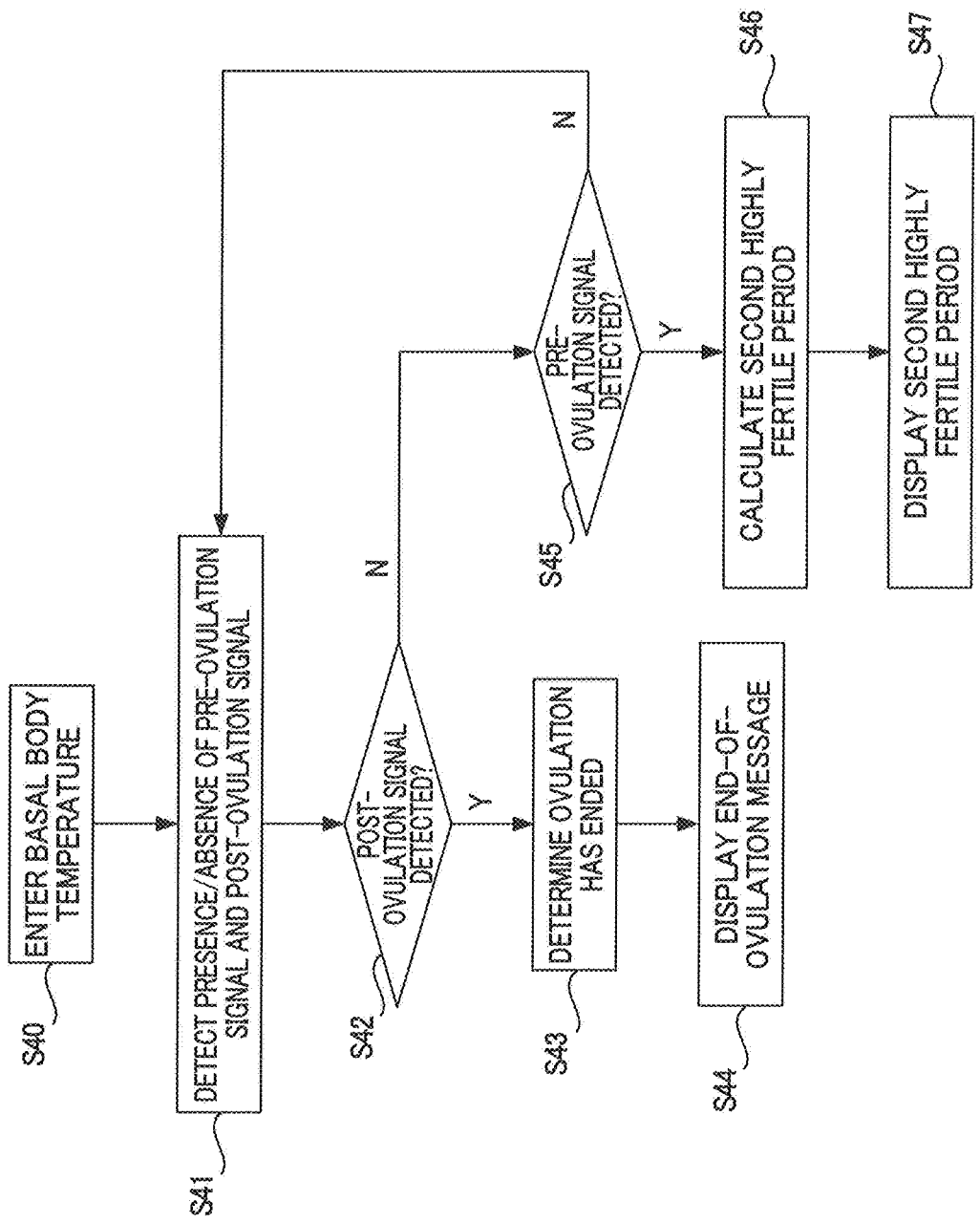
FIG. 9 is a flowchart showing a process of a program according to the fourth embodiment.

Referring to FIGS. 8 and 9, a program according to a fourth embodiment is described. The menstrual cycle and the day of ovulation can vary temporarily depending on, for example, physical conditions of the user. This embodiment describes an example where a highly fertile period (second highly fertile period) that is different from the one obtained in the third embodiment is calculated or an example where the end of ovulation is calculated, using the basal body temperature. Detailed descriptions may be omitted for components and parts similar to those in the first through third embodiments.

Executed on the user terminal 1 by a program according to this embodiment is detection of the presence or absence of a pre-ovulation signal, which indicates a sign before ovulation and/or a post-ovulation signal, which indicates a sign after ovulation, based on the basal body temperature entered a plurality of times through the input unit 1a.

The pre-ovulation signal and the post-ovulation signal can be detected based on the basal body temperature. Various methods can be used for the detection of the pre-ovulation signal and the post-ovulation signal.

Pre-ovulation signals can be detected by performing the following three steps in the program: (1) smoothing the basal body temperature recorded every day using a moving average of every three days; (2) detecting that the smoothed basal body temperature rises in three or, more consecutive days; and (3) judging that the rise in (2) is not the one that has occurred on or before the day that is 17 days prior to [the menstrual cycle of the user plus 1 day]. Alternatively, the detection of the pre-ovulation signal can be made by automatically generating, using a program, a statistical model of variation in basal body temperature during the follicular phase to detect a characteristic pattern prior to ovulation based on it. More specifically, a process of generating a stochastic model for estimating average and variance values of the variations in the follicular phase of the user for every number of days is executed in the program on the user terminal 1. A basic pattern of variation of the follicular phase can be obtained from this model. A process of determining that a sign prior to ovulation has occurred is executed in the program on the user terminal 1, when a variation out of such pattern has found. Parameters indicating what kind of variation is detected with what degree of accuracy can be determined in advance by, for example, analyzing large-scale data.

On the other hand, the post-ovulation signal can be detected using, for example, the coverline calculation method. More specifically, a process of determining that a post-ovulation signal is detected is executed in the program on the user terminal 1 when an increase in body temperature by at least 0.3 degrees from an average body temperature during the period from 11 days after the first day of the last menstruation to the day before is detected based on the basal body temperature recorded daily.

Furthermore, when the pre-ovulation signal is detected, a process calculating the second highly fertile period is executed in the program according to this embodiment on the user terminal 1 based on the pre-ovulation signal. On the other hand, when the post-ovulation signal is detected, a process of determining that the ovulation has ended is executed in the program according to this embodiment on the user terminal 1 based on the post-ovulation signal.

FIG. 8 is a histogram showing the frequencies of occurrence of the pre-ovulation signals (indicated by diagonal hatching from upper left to lower right) and the post-ovulation signals (indicated by diagonal hatching from upper right to lower left) relative to the day of ovulation. The vertical axis represents the frequency and the horizontal axis represents the number of days reckoned from the day of ovulation (0). Cross-hatching corresponds to overlap of the histogram bars.

As can be seen from this graphical representation, the pre-ovulation signal is remarkably detected from 6 days before the day of ovulation and decreases 4 days after the day of ovulation and later. In contrast, the post-ovulation signal is remarkably detected after the day of ovulation. It can be seen that it is highly possible that ovulation will occur in about 10 days from the day on which the pre-ovulation signal is detected. On the other hand, it can be seen that it is highly possible that ovulation has ended on the day when the post-ovulation signal is detected.

The program according to this embodiment is constructed based on, for example, data represented by the aforementioned histogram. As a specific example, executed in the program on the user terminal 1 is a process of calculating a period as the highly fertile period (second highly fertile period) by adding 10 days to the day on which the pre-ovulation signal is detected. On the other hand, a process of determining that the ovulation has ended is executed in the program on the user terminal 1 on the day when the post-ovulation signal is detected.

When the pre-ovulation signal is detected, a process of displaying the second highly fertile period on the display unit 1b is executed in the program on the user terminal 1. How the second highly fertile period is displayed is not specifically limited. Furthermore, the second highly fertile period may be displayed along with the predicted ovulation day data calculated in the first and second embodiments or with the first highly fertile period calculated in the third embodiment. Alternatively only either of them may be displayed. It should be noted that means to present the second highly fertile period to the user is not limited to the display.

When the post-ovulation signal is detected, a process of displaying on the display unit 1b a message indicating that the ovulation has ended is executed in the program on the user terminal 1. How the end message is displayed is not specifically limited. In addition, means to present the end message to the user is not limited to the display.

The program can be configured to detect either one of the pre-ovulation signal and the post-ovulation signal. In such a case, either one of the process of calculating the second highly fertile period and the process of determining the end, of the ovulation is executed in the program on the user terminal 1.

Furthermore, based on the pre-ovulation signal, a process of modifying the first highly fertile period may be executed in the program on the user terminal 1 rather than presenting the second highly fertile period. As a specific example, when the pre-ovulation signal is detected before the first highly fertile period, a process of calculating a combined period of the first highly fertile period and the second highly fertile period as a modified period (third highly fertile period) is executed in the program on the user terminal 1.

Next, referring to FIG. 9, an example is described where the program according to this embodiment is executed on the user terminal 1. Although only the process with the basal body temperature is described here, it can be executed by appropriately combining with the first through third embodiments, as described above.

The user starts the mobile application on the user terminal 1 and enters her daily basal body temperature (S40).

The user terminal 1 detects the presence or absence of the pre-ovulation signal and the post-ovulation signal based on the basal body temperatures entered at S40 (S41).

If the post-ovulation signal is detected (Y at S42), the user terminal 1 determines that the ovulation has ended prior to the day on which the post-ovulation signal is detected (S43).

The user terminal 1 displays on the display unit 1b a message indicating that the ovulation has ended based on the determination result at S43 (S44).

On the other hand, if the post-ovulation signal is not detected and the pre-ovulation signal is detected (Y at S45), the user terminal 1 calculates a period corresponding to 10 days from the day on which the pre-ovulation signal is detected as the second highly fertile period (S46).

The user terminal 1 displays the second highly fertile period calculated at S46 on the display unit 1b (S47).

While the example where the presence or absence of the pre-ovulation signal is determined only when the post-ovulation signal is absent is described with reference to FIG. 9, the present invention is not limited thereto. For example, the calculation of the second highly fertile period may be performed based only on the presence or absence of the pre-ovulation signal (without considering the presence or absence of the post-ovulation signal).

With the program according to this embodiment, the data (the second highly fertile period or the end of ovulation) can be calculated in consideration with, for example, current physical conditions based on the basal body temperature. Accordingly, it is possible to provide a more reliable prediction of the day of ovulation and present the highly fertile period, allowing improvement of the probability of pregnancy.

<Others>

The user terminal 1 may send the menstrual day data and the ovulation day data received in the aforementioned embodiments to the server 2. The server 2 can build a program with a higher accuracy by storing the data thus transmitted in the database 2a and reflecting the data to a conventional program. The program built is distributed to the user terminal 1 as, for example, an upgraded version of the mobile application.

The aforementioned embodiments can be achieved by executing the various processes described above on a computer or a micro-processor by a program. In such a case, all processes may be executed by a program or programs, or one or more processes may be processed by hardware and the remaining process(es) is/are processed by a program or programs. Furthermore, it is possible to supply a program to a computer using a non-transitory computer readable medium with an executable program recorded thereon. Examples of the non-transitory computer readable medium include a magnetic recording medium (such as a flexible disk, a magnetic tape, and a hard disk drive), and CD-ROM (Read Only Memory).

While some embodiments of the present invention have been described, these embodiments are provided as examples and are not intended to limit the scope of the invention. These embodiments can appropriately be combined to practice, and various omissions, substitutions, and modifications can be made without departing from the spirit of the present invention. These embodiments and their modified versions are encompassed in the scope and spirit of the invention and also fall within the scope of the invention described in claims and the equivalents thereof.

DENOTATION OF REFERENCE NUMERALS

1 user terminal
2 server

What is claimed is:

1. A method of predicting a day of ovulation for a person, the method using a user terminal operatively connected to a server, the user terminal having a display unit, the method comprising:
    calculating a particular menstrual cycle of the person based on menstrual day data which have been entered a plurality of times through an input unit of the user terminal, wherein the user terminal is a mobile terminal including one of a smartphone, a tablet computer, or a personal computer,
    calculating, for each of a plurality of menstrual cycles, a period between a menstrual day and a day of ovulation of the person, based on ovulation day data and the menstrual day data, the ovulation day data and the menstrual day data having been entered a plurality of times via the one of the user terminal or the server through the input unit, to calculate a difference between a maximum value and a minimum value of each of the plurality of periods, calculating with one of the user terminal or the server a predicted ovulation day data corresponding to the particular menstrual cycle of the person by applying the particular menstrual cycle to a relationship between an average value of a period between a menstrual day and a day of ovulation of a plurality of persons if the difference is greater than a threshold value, wherein each of the plurality of persons has a same average menstrual cycle length as each other, the relationship being estimated based on large-scale data of the plurality of persons which have been previously obtained, wherein the large-scale data is collected by the server that is configured to store the large-scale data, calculating, in the calculation of the predicted ovulation day data, the predicted ovulation day data based on the plurality of periods between the menstrual day and the day of ovulation if the difference is equal to or smaller than the threshold value, and displaying the predicted ovulation day data on the display unit of the user terminal, wherein the data of the plurality of persons are collected and available via services for personal use, which are provided as a mobile application or a web page and are recorded and managed in a database included in the server, wherein an amount of data of the plurality of persons which the server can collect is greater than one thousand data points.

2. The method according to claim 1 comprising:

calculating a first highly fertile period based on data related to a rate of pregnancy around the day of ovulation based on the data of the plurality of persons which have been previously obtained and the calculated predicted ovulation day data.

3. The method according to claim 2 comprising:

displaying the first highly fertile period on the display unit of the user terminal, wherein the user terminal is one of the smartphone, the tablet computer, or the personal computer.

4. The method according to claim 3 comprising:

detecting a presence or absence of a pre-ovulation signal or a post-ovulation signal based on basal body temperatures which have been entered a plurality of times through the input unit of the user terminal, the pre-ovulation signal indicating a sign before ovulation, the post-ovulation signal indicating a sign after ovulation; and calculating, if the pre-ovulation signal is detected, a second highly fertile period based on the pre-ovulation signal, and determining, if the post-ovulation signal is detected, that the ovulation has ended based on the post-ovulation signal.

5. The method according to claim 2 comprising:

detecting a presence or absence of a pre-ovulation signal or a post-ovulation signal based on basal body temperatures which have been entered a plurality of times through the input unit of the user terminal, the pre-ovulation signal indicating a sign before ovulation, the post-ovulation signal indicating a sign after ovulation; and calculating, if the pre-ovulation signal is detected, a second highly fertile period based on the pre-ovulation signal, and determining, if the post-ovulation signal is detected, that the ovulation has ended based on the post-ovulation signal.

6. The method according to claim 5 comprising:

displaying the second highly fertile period or a message indicating that ovulation has ended on the display unit of the user terminal.

\* \* \* \* \*